United States Patent [19]
DeLuca et al.

[11] Patent Number: 5,089,647
[45] Date of Patent: Feb. 18, 1992

[54] METHOD FOR PREPARING INTERMEDIATES FOR THE SYNTHESIS OF STEROID SIDE CHAINS IN OPTICALLY ACTIVE FORM

[75] Inventors: Hector F. DeLuca, Deerfield; Heinrich K. Schnoes; Kato L. Perlman, both of Madison, all of Wis.

[73] Assignee: Wisconsin Alumni Research Foundation, Madison, Wis.

[21] Appl. No.: 507,971

[22] Filed: Apr. 11, 1990

Related U.S. Application Data

[62] Division of Ser. No. 321,416, Mar. 9, 1989, abandoned.

[51] Int. Cl.$^5$ .................. C07C 315/02; C07C 315/04
[52] U.S. Cl. .................................... 556/428; 560/20; 560/106; 560/254; 568/28; 568/31; 568/32; 568/34; 568/35
[58] Field of Search ........................ 568/28, 31–32, 568/35, 34; 556/428; 560/20, 106, 254

[56] References Cited

PUBLICATIONS

Perlman et al., J. Chem. Soc. Chem. Commun., (16), pp. 1113–1115 (1989).
Fieser, *Reagents for Organic Synthesis*, vol. 3, p. 194 (1972).
Morrison and Boyd, *Organic Chemistry*, 4th ed. (1983), p. 159.
Axelrod, J. Am. Chem. Soc. 90, p. 4385 (1968).
Solladie, Synthesis 8, p. 185 (1981).
Solladie, Chimia 48, 233 (1984).
Drabowicz, J. Org. Chem. 47, p. 3325 (1982).

*Primary Examiner*—Mukund J. Shah
*Assistant Examiner*—Philip Datlow
*Attorney, Agent, or Firm*—Andrus, Sceales, Starke & Sawall

[57] ABSTRACT

This invention provides a novel method for the preparation of optically active arylalykylsulfone derivatives, having a chiral center in the alkyl moiety in either the (R)- or the (S)-configuration. These optically active sulfones find use in the stereospecific synthesis of steroid or vitamin D compounds having chiral center at either carbon 24 or carbon 25 of the side chain. The method comprises the steps of reacting an optically active sulfinate ester having a chiral center at sulfur with a racemic alkyl Grignard reagent to obtain a mixture of diastereomeric sulfoxides, separating the mixture of diastereomeric sulfoxides, and oxidizing separately each of the diastereomers to obtain the desired optically active sulfone.

12 Claims, 3 Drawing Sheets

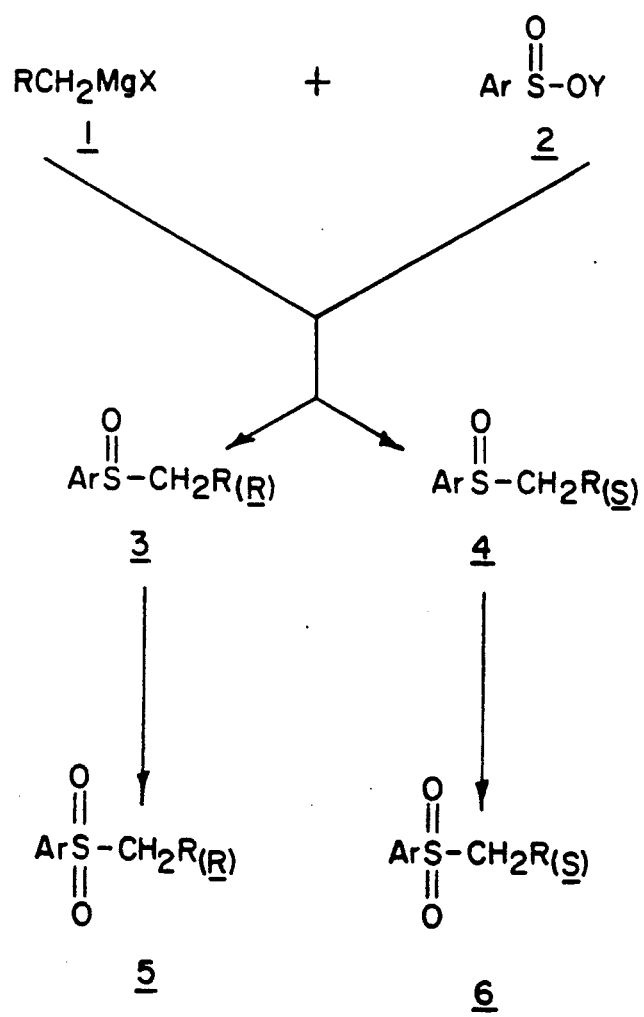

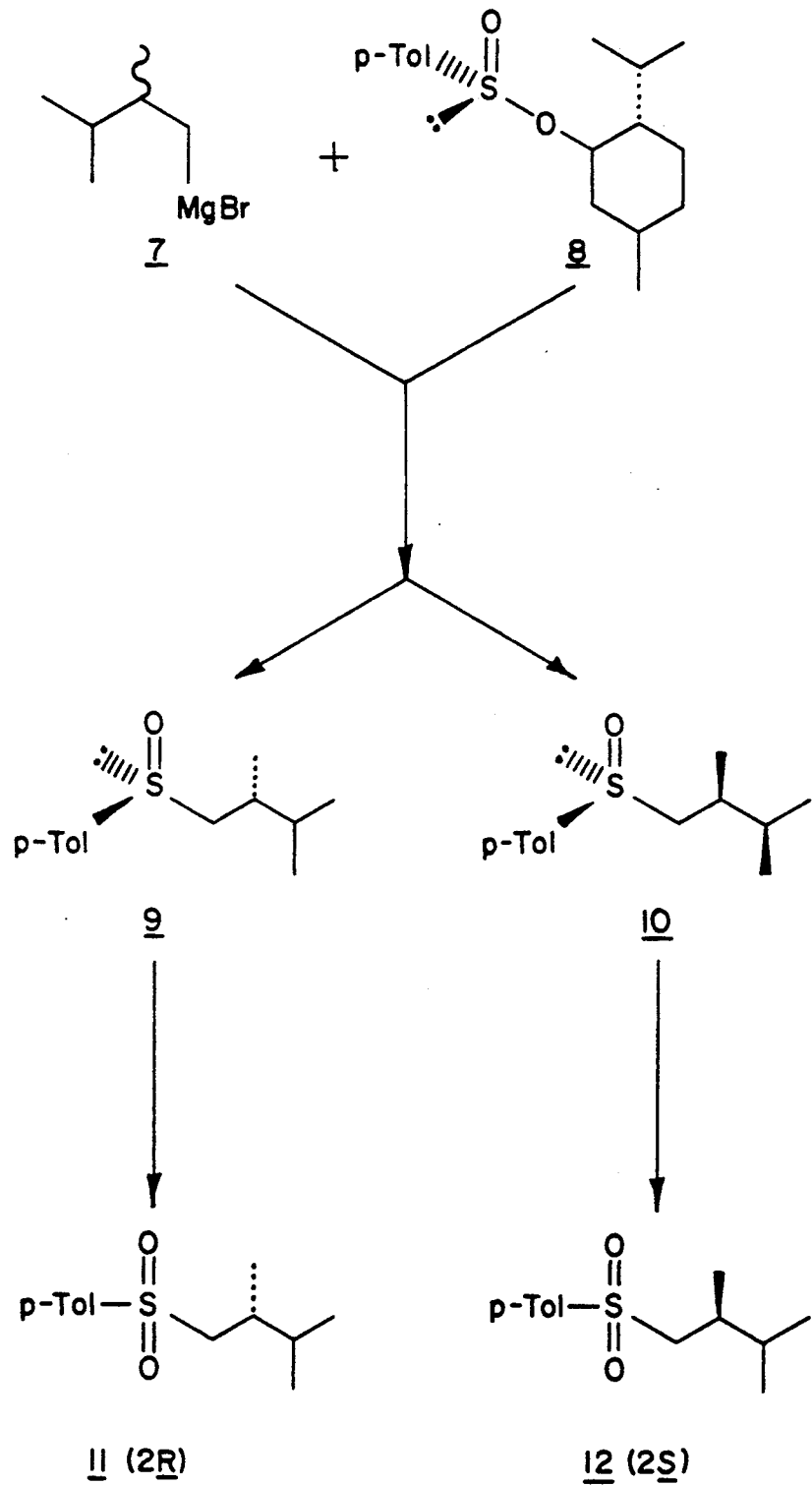

PROCESS SCHEME III
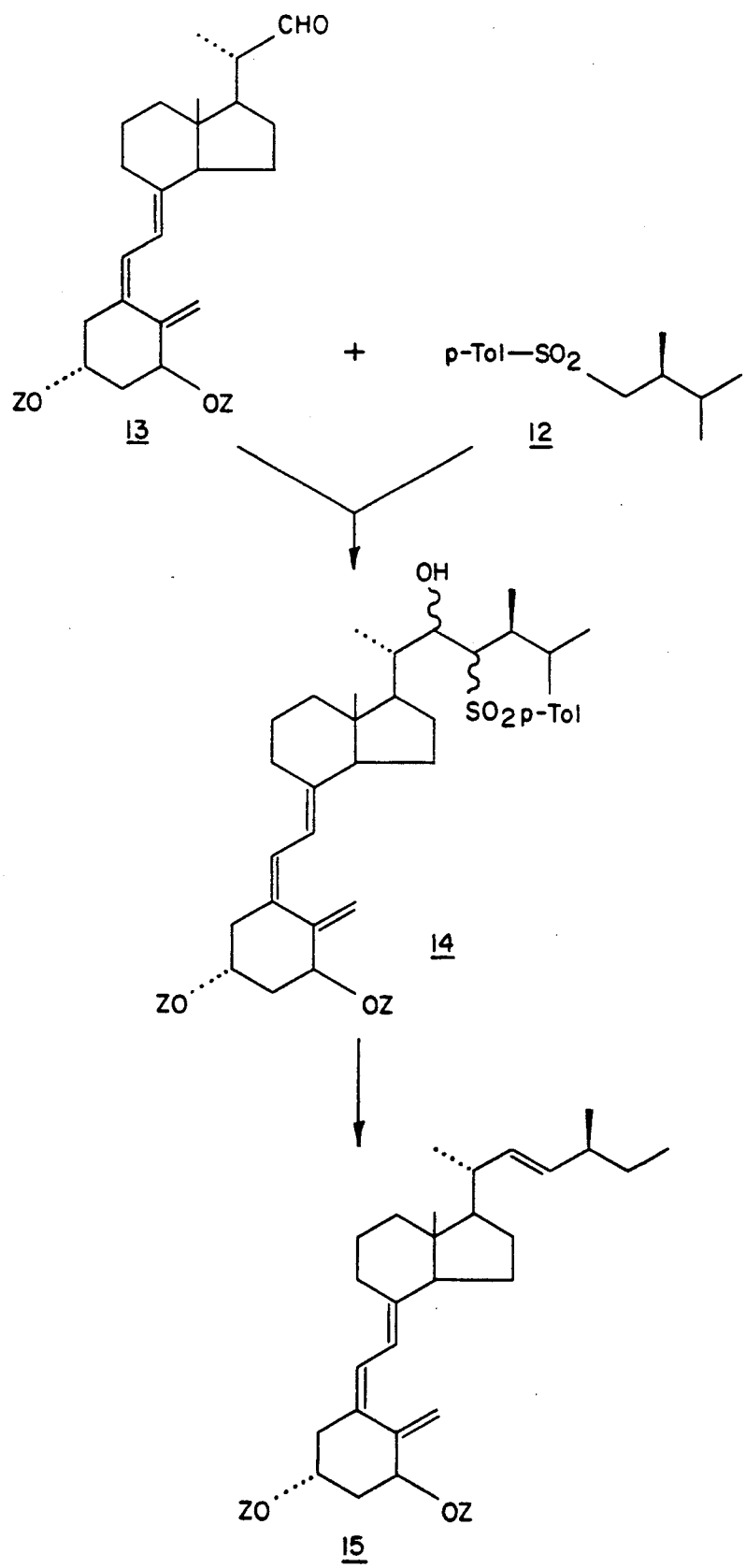

METHOD FOR PREPARING INTERMEDIATES FOR THE SYNTHESIS OF STEROID SIDE CHAINS IN OPTICALLY ACTIVE FORM

This is a divisional of application Ser. No. 07/321,416 filed on Mar. 9, 1989 now abandoned.

This invention was made in the course of work supported by grants or awards from the Department of Health and Human Services. The Government has certain rights in this invention.

This invention relates to a novel method for the synthesis of intermediates that can be used for the construction of steroid side chains. More specifically, the invention relates to the preparation of such intermediates in optically active form.

BACKGROUND

A variety of naturally occurring steroids, and a number of the compounds of the vitamin D series possess side chains with chiral centers at carbon 24 and/or carbon 25. For example, many plant sterols have alkyl substituents (generally methyl or ethyl) at carbon 24, rendering that carbon a chiral center having either the (R)- or (S)-stereochemical configuration. Similarly, various biologically active and medically useful compounds of the vitamin D series feature a methyl or hydroxy substituent at carbon 24, thereby conferring chirality to that center. For example, the known vitamin $D_2$ metabolites, 25-hydroxyvitamin $D_2$ and $1\alpha,25$-dihydroxyvitamin $D_2$, both feature a methyl substituent at carbon 24, and in these compounds that center has the (24S)-configuration. The corresponding (24R)-epimers of these metabolites, wherein the methyl substituent has the opposite orientation, have also been prepared by chemical synthesis. Likewise, vitamin D metabolites or analogues are known containing a chiral center at carbon 25—such as, for example, 25,26-dihydroxyvitamin $D_3$, or 1,25-dihydroxy-26-homovitamin $D_3$ (U.S. Pat. No. 4,717,721).

It is known that the exact stereochemistry of side chain substituents can have a profound effect on the biological properties of steroids and specifically of vitamin D compounds. Hence, in cases where two stereoisomers are possible, it is generally desirable to prepare specifically one or the other of the two, but not a mixture of both. For the case steroid and vitamin D side chain construction, the specific synthesis of one stereoisomer in preference to the other often requires quite elaborate chemical procedures designed to assure the selective formation of one epimer, or else requires the use of laborious and inefficient separation procedures when both stereoisomers are formed in a given reaction sequence.

One of the known methods for the construction of side chains in steroid or vitamin D compounds [e.g. Kutner et al., J. Org. Chem. 53, 3450 (1988)] comprises the condensation of an aryl sulfonyl derivative of the type, $ArSO_2CH_2R$ (where Ar signifies an aryl group, and $CH_2R$ is an alkyl or substituted alkyl group as more fully defined below) with a steroid or vitamin D-22-aldehyde, as illustrated by the transformation below:

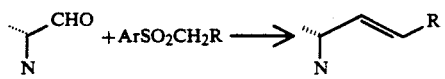

where N is the steroid or vitamin D nucleus. Similarly, condensation of the same sulfone with a steroid or vitamin D-22-tosylate gives the corresponding saturated side chain structure according to the reaction:

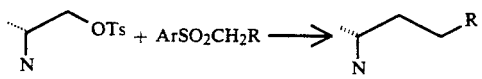

It is readily apparent that by variations in the structure of the $CH_2R$ unit, a large range of different side chains may be constructed by means of the above condensation processes. It is also apparent that if the desired steroid or vitamin D side chain is to contain a chiral center within R (as, for example, at carbon 24 or 25), having a specific stereochemical orientation (i.e. (R) or (S), but not both), then the use of an optically active $ArSO_2CH_2R$ reactant in the above-illustrated condensation process, having a chiral center with that desired stereochemical orientation in the R-moiety would be highly advantageous. The alternative, namely the use of a racemic $ArSO_2CH_2R$ reactant (i.e. one in which the chiral center within R is present in both the (R)- and (S)-configuration) would lead to the formation of two epimers of the final steroid or vitamin D product, whose separation may be very difficult and laborious, or impossible by current methods. Hence, in cases where only one chiral form of a side chain is desired, the efficient use of synthons of the type $ArSO_2CH_2R$ for side chain construction according to the above-indicated processes, requires the preparation of these sulfonyl synthons in optically active forms—i.e. as the pure (R) or (S)-epimers, but not a mixture of both.

In previous work certain phenylalkylsulfonyl derivatives have been prepared in optically active form, but these preparations involved elaborate and multistep procedures [Mori et al., Tetrahedron 38, 2099 (1982); Sakahabara et al., Heterocycles 17, 301 (1982); Feraboschi and Santaniello, Synth. Commun. 14, 1199 (1984); Kociensky et al., J. Chem. Soc. Perkin Trans. 1, 834 (1978); Masamune et al., J. Am. Chem. Soc. 107, 4549 (1985)].

Thus, in view of the practical medical importance of specific steroid side chain stereoisomers—especially in the vitamin D series—there exists a need for methods providing for the convenient preparation of appropriate side chain units in optically active form.

BRIEF DESCRIPTION OF THE DRAWINGS

FIG. 1 (Process Scheme I) illustrates in general a process for preparing optically active sulfone synthons from optically active sulfinate esters;

FIG. 2 (Process Scheme II) illustrates a specific example for preparing 2R and 2S-2,3-Dimethylbutyl-p-tolylsulfone in accordance with the general procedure illustrated in FIG. 1; and FIG. 3 (Process Scheme III) illustrates one example of the use of an optically active sulfone synthon prepared by the process of FIG. 1 for the construction of a chiral side chain in a vitamin D compound.

DISCLOSURE OF INVENTION

This invention provides a novel and efficient procedure for the preparation of chiral side chain synthons in either the (R) or (S) stereochemical forms. These side chain synthons can then be used according to known methods for the construction of steroid or vitamin D side chains with chiral centers at the carbon 24 or carbon 25 positions. Specifically, this invention provides novel sulfone derivatives of the type:

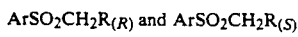

where Ar is an aryl group, and $R_{(R)}$ is an alkyl or substituted alkyl radical containing a chiral center that has the (R)-stereochemical configuration, and $R_{(S)}$ represents an alkyl or substituted alkyl radical containing a chiral center in the (S)-stereochemical configuration. The exact nature of the Ar group is not critical, but preferably represents one of the simple arene moieties, for example a phenyl, naphthyl, tolyl or methoxyphenyl group, and R is a group as defined by structures A or B shown below:

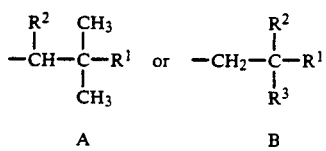

where $R^1$ is selected from the group consisting of hydrogen, hydroxy and protected hydroxy, $R^2$ and $R^3$ are each selected from the group consisting of $C_1$ to $C_4$-alkyl, hydroxymethyl, protected-hydroxy-methyl and trifluoromethyl, except that $R^2$ and $R^3$ cannot be identical, and where the chiral center in A or B has the (R)- or the (S)-configuration.

As used in this specification and the claims, a protected-hydroxy group is a hydroxy function derivatized with any of the common hydroxy-protecting groups such as acyl, $C_1$ to $C_4$ alkylsilyl or alkoxyalkyl groups. An acyl group is an alkanoyl group of 1 to 5 carbons such as formyl, acetyl, propionyl, etc., or an aromatic acyl group, such as benzoyl or a nitro, halo- or methyl-substituted benzoyl group. $C_1$ to $C_4$-alkylsilyl-protecting groups include trimethylsilyl, triethylsilyl, dimethylethylsilyl, diethylmethylsilyl, isopropyldimethylsilyl and t-butyldimethylsilyl, and alkoxyalkyl-protecting groups include methoxymethyl, ethoxymethyl, methoxyethoxymethyl, tetrahydrofuranyl and tetrahydropyranyl groupings. For the purposes of the present process, the $C_1$ to $C_4$-alkylsilyl or alkoxyalkyl groups are preferred hydroxy-protecting groups.

It is apparent from the above structures that the coupling of a sulfone $ArSO_2CH_2R$, where R represents a radical of structure A, with a suitable steroid or vitamin D nucleus provides the steroid or vitamin D product having a side chain with a chiral center at carbon 24, whereas coupling of a sulfone containing the unit of structure B above, leads to a steroid or vitamin D product containing a chiral center at carbon 25 of the side chain.

The process of this invention takes advantage of the fact that optically active sulfinate esters, having a chiral center at sulfur, have been prepared and are commercially available, and that such sulfinate esters are known to react with Grignard reagents with inversion of stereochemistry so as to form optically active sulfoxides having a chiral center at sulfur of a stereochemistry inverted with respect to that of the original sulfinate ester [see e.g. Axelrod et al., J. Am. Chem. Soc. 90, 4835 (1968); Drabowicz et al., J. Org. Chem. 47, 3325 (1982); Solladie, Synthesis 8, 185 (1981); Solladie, Chimia 48, 233 (1984)]. The process of the present invention makes use of this known chemistry to achieve the formation of diastereomeric sulfoxides which can be separated and then further oxidized to the desired optically active sulfones illustrated above.

The new process for preparing these optically active sulfone synthons is illustrated in general form by the reaction series depicted in Process Scheme I. The process comprises two reactions and a separation step. The first step of the process is a Grignard reaction conducted in an organic solvent, such as an ether solvent or benzene, between a racemic Grignard reagent represented by general structure 1 and a optically active sulfinate ester of general structure 2. In the Grignard reagent, R is a hydrocarbon or substituted hydrocarbon group as defined above, having a chiral center in both the (R)- and the (S)-configuration (thus rendering the compound racemic), and X represents a halogen atom, e.g. chlorine, bromine or iodine.

In the optically active sulfinate ester of structure 2, Ar represents an aryl group as defined above, and Y is a alkyl or cycloalkyl group (more fully defined below), and the sulfur atom is a chiral center which may have either the (R)- or the (S)-configuration.

The sulfur chirality of sulfinate esters of structure 2 may be more specifically illustrated by the structures below:

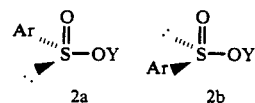

where structure 2a represents the sulfinate ester having a chiral center at sulfur in the (R)-configuration, whereas structure 2b shows the sulfinate ester having a chiral sulfur center in the (S)-configuration. In these structures, the symbols ———: or ......: represent a non-bonded (lone) electron pair.

For purposes of the process of this invention, sulfinate esters having either the (R)- or the (S)-configuration at sulfur (i.e. either compounds of type 2a or 2b shown above) can be used. Such optically active sulfinate esters are known compounds and examples highly suitable for the present process commercially available (e.g. from Aldrich Chemical Co., Milwaukee, Wis.).

The above described Grignard reaction between compounds 1 and 2 leads, as shown in Process Scheme I, via displacement of the —OY group in the sulfinate ester, to a mixture of two products, namely the sulfoxides of structure 3 and 4, respectively. In these structures, Ar represents an aryl residue as previously defined, and R is a group as defined above, whereby the designations $R_{(R)}$ and $R_{(S)}$ signify that the chiral center in R has the (R)- or the (S)-configuration, respectively, and the sulfur atom in these sulfoxides also is a chiral center that has either the (R)- or the (S)-configuration. The Grignard reaction occurs with inversion of stereochemistry at sulfur, i.e. the sulfur center in sulfoxides 3 and 4 has a stereochemical configuration inverted with respect to the sulfur center in the precursor compound 2. Thus, for example, reaction of the sulfinate ester having the (R)-stereochemistry at sulfur as illustrated by structure 2a above with the racemic Grignard reagent of structure 1, leads to a pair of sulfoxides that may be represented by structures 3a and 4a below:

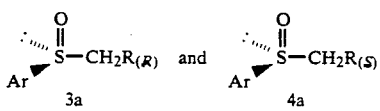

For the success of the present process the important consequence of the Grignard reaction is that sulfoxides 3 and 4 both have the same chirality at the sulfur center, but a chiral center of opposite stereochemical orientation within the group R, as designated by the notation $R_{(R)}$ and $R_{(S)}$ for the R group in compounds 3 and 4, respectively. Hence, these compounds are diastereomers of each other and as such can be resolved by column chromatography or high pressure liquid chromatography (hplc) to obtain separately the sulfoxide 3 having the (R)-chiral center in R, and the sulfoxide 4 having the corresponding (S)-chiral center in the group R.

After separation, either one, or both (depending on whether one or both of the enantiomers are desired) of the sulfoxides 3 and 4 are then individually oxidized with an organic peracid (e.g. perbenzoic acid or similar per-acids), to obtain the desired optically active sulfones of structure 5 and 6, respectively, the former, as designated by the notation $R_{(R)}$ having the (R)-configuration at the chiral center in R, the latter, as indicated by the notation $R_{(S)}$, having the (S)-configuration at that center. In products 5 and 6, the sulfur center, having been oxidized to a sulfone, has, of course, lost its chirality. Thus, the process of this invention achieves in effect the transformation of an optically active sulfinate with chirality at sulfur to an optically active sulfone with chirality in the alkyl group R of the molecule. These sulfones of type 5 and 6 can then be used directly in the known side chain condensation processes illustrated above, for the construction of chiral steroid or vitamin D side chains, thus permitting the synthesis of steroid or vitamin D compounds having either the (R)- or (S)-configuration at either carbon 24 or carbon 25 of their side chains.

The racemic Grignard reagents of general structure 1, used in the above process, are conveniently prepared by standard methods from the corresponding racemic halides, according to the reaction:

where R and X represent alkyl and halogen groups, respectively, as previously defined. In general and as is typical for Grignard reactions, these Mg-Grignard reagents are generated in situ immediately prior to reaction with the sulfinate ester 2. The alkyl or substituted alkyl-halides of general structure $RCH_2X$ above are either commercially available, or can be prepared readily by known methods, e.g. from the corresponding alcohols of general structure $RCH_2OH$, which in turn, if not available per se, can be obtained from the corresponding esters or from suitable terminal olefins.

Representative examples of racemic Grignard reagents that can be used in the process of this invention, and of the chiral sulfone derivatives that can be produced from them by the reaction sequence of Process Scheme I are illustrated by the entires (a) to (h) below.

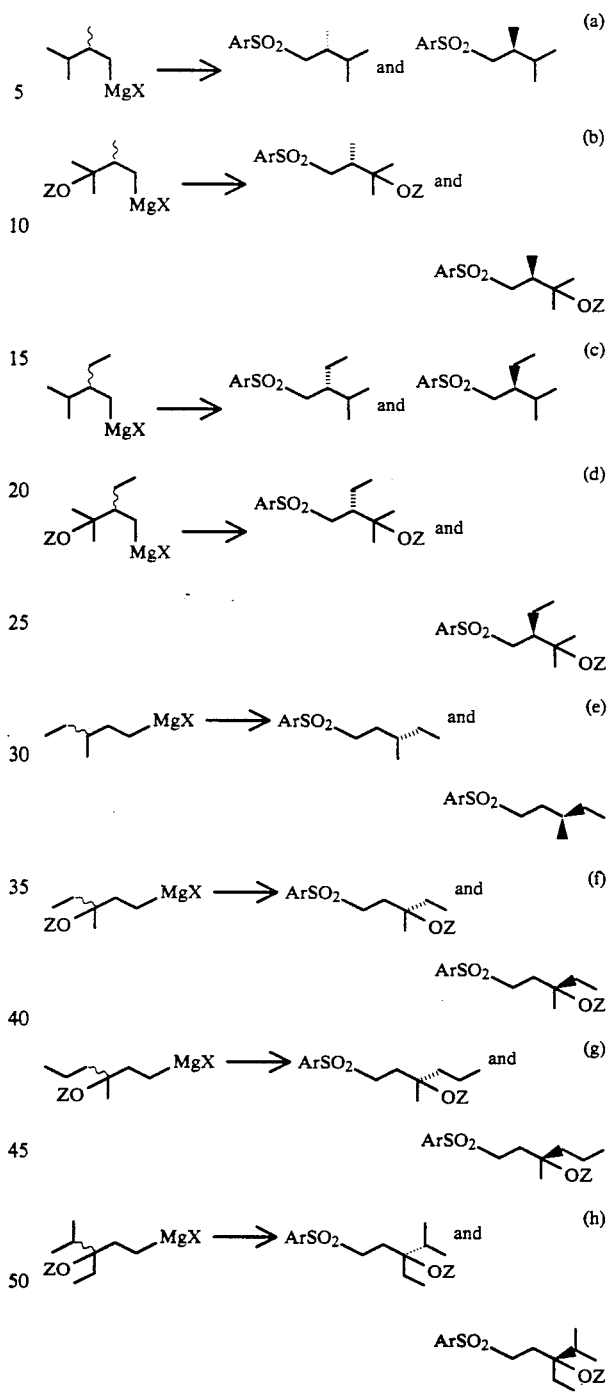

In these examples, Ar and X represent groups as previously defined, and Z represents a hydroxy-protecting group, preferably a $C_1$ to $C_4$-alkylsilyl or alkoxyalkyl group as previously defined.

As stated above, the sulfinate ester of structure 2 to be used in the process of this invention must have either the (R)-or the (S)-configuration at the sulfur center (i.e. it must have a structure as represented by stereostructures 2a or 2b above), either isomer being equally useful, and either isomer being usable in the process under analogous experimental conditions with equivalent results. In sulfinate esters of general structure 2, Ar may be any aryl group, preferably a phenyl, naphthyl, toluene or methoxyphenyl group. In sulfinate esters of general structure 2, Ar may be any arene group, preferably a phenyl, naphthyl, toluene or methoxy chiral center, the group Y in these sulfinate esters may represent a broad range of structures, i.e. Y may be any alkyl or cycloalkyl group. In the context of the present process, an 'alkyl or cycloalkyl group' denotes any aliphatic or alicyclic, saturated or unsaturated, hydrocarbon radical of 1 to 30 carbons, which, additionally, fulfills the conditions that, when present as Y in sulfinate esters of structure 2, it renders such sulfinate esters soluble in benzene or ether solvents, and does not react or complex with Grignard reagents. Preferred examples of such groups include cyclic hydrocarbons having one or more rings, such as cyclopentyl, cyclohexyl, which also may contain one or more $C_1$ to $C_5$ alkyl substituents, such as methyl, ethyl, propyl, isopropyl, t-butyl, etc. Other preferred examples of alkyl or cycloalkyl groups are monoterpenoid hydrocarbon radicals (e.g. menthyl, fenchyl, norbornyl) or higher terpenoid or steroid hydrocarbon groups. A number of chiral sulfinate esters of structure 2 have been prepared and in these known compounds (for reasons relating to ease of preparation in optically active form), the alkyl group Y generally itself contains one or more chiral centers of known configuration. For example, a commercially available sulfinate ester highly suitable for the present process is (−)-menthyl (+)(R)-p-toluenesulfinate, i.e. the compound of structure 2, where Ar is a toluene group and Y is a (−)-menthyl radical, and where the chiral center at sulfur has the (R)-configuration, as represented explicitly in structure 2a above. The corresponding (S)-toluene-sulfinate ester is also available.

The process of this invention is more specifically described by the examples below, which are intended to be illustrative only and do not reflect the full scope of the invention as defined in the claims. In these examples, the designation of intermediates or products by Arabic numerals (e.g. compounds 7, 8, 9, etc.) refer to the structures so numbered in the appended Process Scheme II.

EXAMPLE 1

(2R)-2,3-Dimethylbutyl-p-tolylsulfoxide (9) and (2S)-2,3-dimethyl-p-tolylsulfoxide (10)

Magnesium turnings (0.24 g, 10 mmol) and a crystal of $I_2$ were placed in a dry flask and covered with 5.0 mL of anhydrous tetrahydrofuran. 1-Bromo-2,3-dimethylbutane (1.54 g, 8 mmol) [prepared by known procedures, e.g. see Martinez et al. Gazz. Chim. Ital. 97, 96 (1967); Tsuda et al. J. Am. Chem. Soc. 82, 3396 (1960); Organic Synth. Coll. Vol. 2, p. 358, A. H. Blatt, ed., Wiley & Sons, N.Y. (1943)] was added slowly with stirring under nitrogen atmosphere and occasional cooling. The mixture was stirred at room temperature for 1.5 h or until most of the magnesium was consumed. This mixture (containing compound 7) was cooled and 2.35 g (R)-(+)-p-toluenesulfinic acid (−)-menthyl ester (compound 8) (10 mmol) in 10.0 mL of anhydrous tetrahydrofuran was added. The mixture was stirred under nitrogen atmosphere at room temperature for 16 h, cooled and decomposed with saturated $NH_4Cl$ solution. The organic layer was separated and the aqueous phase extracted several times with ether. The combined organic phase was washed with water and brine, dried with $MgSO_4$, filtered and evaporated. The residue was chromatographed on a 70-270 mesh silica gel column to give 1.26 g of diastereomeric sulfoxide mixture. This was separated by flash chromatography on a 230-400 mesh silica gel column with ethyl acetate and hexane mixtures or by semipreparative HPLC (Zorbax Sil, 9.4×25 cm column) using ethyl acetate-hexane mixtures. The first compound to elute was the (S)-(−)-p-tolyl-(2R)-2,3-dimethylbutylsulfoxide (9) and the second compound was the (S)-(−)-p-tolyl-(2S)-2,3-dimethylbutyl sulfoxide (10). MS m/z (relative intensity 224 (M+, 6), 208 (14), 140 (100), 139 (8), 124 (30), 92 (22), 91 (21), 44 (10), 43 (71), 28 (34), 27 (25); $^1$H NMR (CDCl$_3$) δ0.80 (3H, d, J=7.0 Hz), 0.89 (3H, d, J=7.0 Hz), 0.98 (3H, d, J=6.5 Hz), 1.6-1.82 (2H, m), 2.42 (3H, s, CH$_3$-Ar), 2.71 (2H, m), 7.34 (2H, d, J=15 Hz) (H-aryl ortho), 7.54 (2H, d, J=15 Hz, H-aryl ortho). (2S) sulfoxide 10 $[\alpha]_D^{20}$ = −153.5 (c=4 in CHCl$_3$); (2R) sulfoxide 9 $[\alpha]_D^{20}$ = −444.8 (c=4 in CHCl$_3$). Anal. calcd. for C$_{13}$H$_{20}$OS: C, 69.59; H, 8.99; S, 14.29. Found 9: C, 69.63; H, 8.95; S, 14.34. 10:C, 69.69; H, 9.01; S, 14.31.

EXAMPLE 2

(2S)-2,3-Dimethylbutyl-p-tolylsulfone (12)

(2S)-2,3-Dimethylbutyl-p-tolylsulfoxide (10) (52 mg, 0.2 mmol) was dissolved in 1.0 mL of anhydrous dichloromethane and 60 mg (0.3 mmol) of 3-chloroperoxybenzoic acid (80–85%, Sigma) added with stirring. The reaction mixture was stirred for 2 h and quenched with 10% sodium bicarbonate. More dichloromethane was added and the combined organic extracts were washed with aqueous sodium sulfite and brine and dried with $MgSO_4$. The solvent was removed in vacuo and the crude sulfone was purified by silica gel flash chromatography using hexane ethyl acetate mixtures to afford sulfone (12) as a colorless oil. For analytical purposes this was also purified by HPLC (Zorbax Sil 9.4×25 cm column) using 10% ethyl acetate in hexane to give 42 mg of pure (2S)-sulfone (12): $[\alpha]_D^{20}$ = +17 (c=3.5 in CHCl$_3$); MS m/z (relative intensity) 240 (M+, 3), 197 (5), 157 (100), 92 (19), 91 (27), 85 (25), 84 (31), 43 (72); $^1$H NMR δ0.77 (3H, d, J=7 Hz), 0.82 (3H, d, J=7.0 Hz), 1.00 (3H, d, J=7.0 Hz), 1.66-1.98 (2H, m), 2.45 (3H, s, CH$_3$-Aryl), 2.86 (1H, dd, J=8, 11 Hz), 3.06 (1H, dd, j=4, 12 Hz), 7.35 (2H, d, J=7.0 Hz, H-aryl ortho), 7.75 (2H, d, J=8, H-aryl ortho). Anal. Calcd. for C$_{13}$H$_{20}$O$_2$S: C, 64.96; H, 8.39; S, 13.34. Found C$_{13}$H$_{20}$O$_2$S: C, 65.05; H, 8.37; S, 13.24

EXAMPLE 3

(2R)-2,3-Dimethylbutyl-p-tolylsulfone (11)

The (2R)-sulfone (11) was prepared by oxidation of sulfoxide 9, using the experimental procedure as described in Example 2 above. The resulting (2R) sulfone (11) showed an optical rotation of $[\alpha]_D^{20}$ = −19 (c-1.4, CHCl$_3$).

The following example illustrates the use of the optically active sulfone synthons prepared by the process of this invention for the construction of chiral side chains in vitamin D compounds. Numbered compounds in this example (e.g. compounds 13, 14, 15) refer to the structures so numbered in Process Scheme III.

EXAMPLE 4

(24S)-1α-Hydroxyvitamin D$_2$ (15, Z=H)

To a stirred solution of 30 mg (125 μmol) of (2S)-2,3-dimethylbutyl-p-tolylsulfone (12) in 300 μL anhydrous tetrahydrofurane (containing 1.10-phenanthroline as an indicator) was added under argon at −78° C. 18 μL (130 μmol) of diisopropylamine followed by 86 μL of a solution of n-BuLi in hexane (1.50M, 130 μmol). The solution was stirred at −78° C. for 15 min (dark brown color), and 4 mg (7 μmol) of the protected aldehyde (13 Z=t-BuMe$_2$Si) in 0.3 mL of anhydrous tetrahydrofurane was added and the mixture stirred under argon at −78° C. for 1 h. The reaction mixture was quenched with 1 mL of saturated NH$_4$Cl solution, warmed to 0° C. and extracted with ethyl acetate, and the organic phase was washed with saturated NaCl. The organic phase was dried with MgSO$_4$, filtered and evaporated. The residue was redissolved in ethyl acetate, passed through a Sep Pak column in ethylacetate and evaporated. The residue was purified by HPLC (Zorbax Sil 9.4×25 cm column) using 10% ethylacetate in hexane to give 3.3 mg (58%) of the hydroxysulfones (14, Z=t-BuMe$_2$Si). MS m/z (relative intensity) 812 (M$^+$, 20), 680 (34), 440 (52), 248 (64), 157 (65), 75 (100).

A saturated solution of Na$_2$HPO$_4$ in methanol (1.0 mL) was added to a stirred solution of the 3.3 mg sulfone (14) in 1.0 mL of anhydrous tetrahydrofuran followed by 160 mg of powdered anhydrous Na$_2$HPO$_4$. The mixture was stirred under argon for 15 min. cooled to 0° C. and fresh 5% sodium amalgam (ca. 400 mg) added. The mixture was stirred at 5° C. for 20 h; 5 mL of hexane added and the hexane layer decanted. The solid material was then extracted with 10% ethyl acetate in hexane (3×5 mL). The combined organic phase was washed with saturated NaCl and filtered through a Sep Pak cartridge and evaporated. Final purification on HPLC (Zorbax Sil 9.4×25 cm column) (10% ethyl acetate in hexane as solvent) gave 1.05 mg (40%) of vitamin D$_2$ derivative (15, Z=t-BuMe$_2$Si). (As a by-product, 0.47 mg of the 22-hydroxylated derivative was also obtained.) MS m/z (relative intensity) 640 (M$^+$, 24), 508 (65), 248 (67), 147 (13), 73 (100), 69 (58); $^1$H NMR δ0.54 (3H, s, 18-CH$_3$), 4.19 (1H, m, 3-H), 4.35 (1H, m, 1-H), 4.86 (1H, S, 19Z-H), 5.17 (3H, m, 19E-H and 22-23-H-S), 6.00 (1H, d, J=9.6 Hz, 7-H), 6.23 (1H, d, J=8.8 Hz, 6-H). The hydroxy-protected diol (15, Z=t-BuMe$_2$Si, 800 μg) was dissolved in 0.5 mL of anhydrous tetrahydrofuran, and to this solution was added 90 μL 1M solution of tetrabutylammonium fluoride in tetrahydrofuran. The mixture was stirred under argon at 55° C. for 1 h. The mixture was cooled and 5 mL of ether added. The organic phase was washed with saturated NaCl solution and dried over anhydrous MgSO$_4$, evaporated and redissolved in 20% 2-propanol in hexane and filtered through Sep-Pak. Preparative HPLC (Zorbax-Sil 9.4 mm×25 cm column) in 20% 2-propanol in hexane gave in pure form 308 μg 1α-hydroxy-24-epi-vitamin D$_2$ (15, Z=H). 1α-Hydroxy-24-epi-vitamin D$_2$ exhibited the following spectral properties: UV (EtOH) λ$_{max}$: 264 nm, λ$_{min}$ 228; MS m/z (relative intensity) 412 (M$^+$, 13), 394 (21), 376 (7), 287 (4), 269 (7), 251 (6), 252 (31), 251 (6), 152 (35), 151 (15), 134 (100), 69 (50), 55 (73); $^1$H NMR (CDCl$_3$) δ0.49 (3-H, S, 18-CH$_3$), 0.77 (3-H, d, J=7.1 26 or 27-CH$_3$), 0.85 (3H, d, J=6.8, 28-CH$_3$), 0.94 (3H, d, J=6.5, 21-CH$_3$), 4.94 (1H, S, 19Z-H), 5.13 (2H, m, 22 and 23H) (5.11, 5.13, 5.14), 5.26 (1H, S, 19E-H), 5.99 (1H, d, J=11.2 Hz, 7-H), 6.35 (1H, d, J=11.2 Hz, 6-H), 4.21 (1H, m, 3-H), 4.41 (1H, m, 1-H). 1α-Hydroxy-24-epi-vitamin D$_2$ can be distinguished from the previously known 1α-hydroxyvitamin D$_2$ by reverse phase HPLC (4.6 mm×25 cm, ODS-Zorbax column) with 15% water in acetonitrile. The first compound to elute in this system was 1α-hydroxy-24-epi-vitamin D$_2$ and the second, the known 1α-hydroxyvitamin D$_2$.

As illustrated by the preceding example the stereochemical identity of the sulfone products prepared by the process of this invention can be ascertained by actual use of the products in making a specific steroid or vitamin D derivative which can be correlated or contrasted with other known steroid or vitamin D derivatives. Alternatively, stereochemical orientation can be determined by methods known in the art such as, X-ray crystallography or chemical correlation combined with spectroscopy.

We claim:

1. A process for the preparation of optically active sulfone derivatives having the structure:

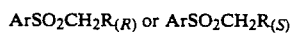

$ArSO_2CH_2R_{(R)}$ or $ArSO_2CH_2R_{(S)}$ where Ar is an aryl group and R is selected from the group consisting of

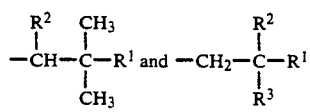

wherein R$^1$ is selected from the group consisting of hydrogen, hydroxy and protected hydroxy, R$^2$ and R$^3$ are each selected from the group consisting of C$_1$ to C$_4$ alkyl, hydroxymethyl, protected-hydroxymethyl and trifluoromethyl, except that R$^2$ and R$^3$ cannot be identical, and where the subscripts (R) and (S) signify that the chiral center in R has the (R) and (S)-stereochemical configuration, respectively, which comprises, reacting a racemic Grignard reagent of the structure,

RCH$_2$MgX where R is a group as defined above and X is a halogen atom, with a chiral sulfinate ester of the structure,

where Ar is a group as defined above, and Y represents an alkyl or cycloalkyl group, and where the sulfur atom is a chiral center having either the (R)- or the (S)-configuration, thereby obtaining a mixture of diastereomeric sulfoxides having the structure,

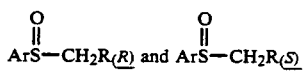

wherein Ar, R and the subscripts (R) and (S) have the meaning as defined above, and where the sulfur atom is a chiral center having either the (R)- or the (S)-configuration, separating that mixture, and oxidizing separately each of the diastereomers with an organic peracid.

2. The process as claimed in claim 1 where R in the Grignard reagent has the structure,

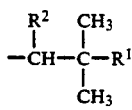

wherein R[1] is selected from the group consisting of hydrogen, hydroxy and protected hydroxy, and R[2] is selected from the group consisting of methyl, ethyl, propyl and isopropyl.

3. The process as claimed in claim 2 where R is selected from the group consisting of 3-methyl-2-butyl and 3-hydroxy-3-methyl-2-butyl in hydroxy-protected form.

4. The process of claim 1 where R in the Grignard reagent has the structure,

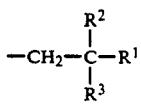

wherein R[1] is selected from the group consisting of hydrogen, hydroxy and protected hydroxy, R[2] and R[3] are each selected from the group consisting of $C_1$ to $C_4$ alkyl, hydroxymethyl, protected hydroxymethyl and trifluoromethyl, except that R[2] and R[3] cannot be identical.

5. The process as claimed in claim 4 where R is selected from the group consisting of 2-methylbutyl, 2-hydroxy-2-methylbutyl in hydroxy-protected form, 2-methylpentyl, 2,3-dimethylbutyl, 2-hydroxy-2-methylpentyl in hydroxy-protected form, 2-ethylpentyl and 2-ethyl-2-hydroxypentyl in hydroxy-protected form.

6. The process according to claim 1 where the sulfinate ester used has a chiral center at sulfur in the (R)-configuration.

7. The process according to claim 1 where the sulfinate ester used has a chiral center at sulfur in the (S)-configuration.

8. The process according to claim 1 where the sulfinate ester is (−)menthyl(+)(R)-toluene sulfinate.

9. The process according to claim 2 where the product obtained has the chiral center in the group R in the (R)-configuration.

10. The process according to claim 2 where the product obtained has the chiral center in the group R in the (S)-configuration.

11. The process according to claim 4 where the product obtained has the chiral center in the group R in the (R)-configuration.

12. The process according to claim 4 where the product obtained has the chiral center in the group R in the (S)-configuration.

* * * * *

UNITED STATES PATENT AND TRADEMARK OFFICE
CERTIFICATE OF CORRECTION

PATENT NO. : 5,089,647
DATED : February 18, 1992
INVENTOR(S) : Hector F. DeLuca et al It is certified that error appears in the above-identified patent and that said Letters Patent is hereby corrected as shown below:

| | |
|---|---|
| Claim 1<br>Column 10, Line 15 | Delete "$ArSO_2CH_2R_{(R)}$ or $ArSO_2CH_2R_{(S)}$" and substitute therefore --- $ArSO_2CH_2R_{(R)}$ or $ArSO_2CH_2R_{(S)}$ --- |
| Claim 1<br>Column 10, Line 31 | Delete "(R) and (S)" and substitute therefore --- $\underline{(R)}$ and $\underline{(S)}$ --- |
| Claim 1<br>Column 10, Line 32 | Delete "(R) and (S)" and substitute therefore --- $\underline{(R)}$ and $\underline{(S)}$ --- |
| Claim 1<br>Column 10, Line 47 | Delete "(R)- or the (S)-" and substitute therefore --- $\underline{(R)}$- or the $\underline{(S)}$- --- |
| Claim 1<br>Column 10, Line 55 | Delete "(R) and (S)" and substitute therefore --- $\underline{(R)}$ and $\underline{(S)}$ --- |
| Claim 1<br>Column 10, Line 57 | Delete "(R)- or the (S)-" and substitute therefore --- $\underline{(R)}$- or the $\underline{(S)}$- --- |
| Claim 6<br>Column 12, Line 5 | Delete "(R)" and substitute therefore --- $\underline{(R)}$ --- |

UNITED STATES PATENT AND TRADEMARK OFFICE
CERTIFICATE OF CORRECTION

PATENT NO. : 5,089,647
DATED : February 18, 1992
INVENTOR(S) : Hector F. DeLuca et al It is certified that error appears in the above-identified patent and that said Letters Patent is hereby corrected as shown below:

| | |
|---|---|
| Claim 7 Column 12, Line 8 | Delete "(S)" and substitute therefore --- (S) --- |
| Claim 8 Column 12, Line 11 | Delete "(R)" and substitute therefore --- (R) --- |
| Claim 9 Column 12, Line 14 | Delete "(R)" and substitute therefore --- (R) --- |
| Claim 10 Column 12, Line 17 | Delete "(S)." and substitute therefore --- (S) --- |
| Claim 11 Column 12, Line 20 | Delete "(R)" and substitute therefore --- (R) --- |

UNITED STATES PATENT AND TRADEMARK OFFICE
CERTIFICATE OF CORRECTION

PATENT NO. : 5,089,647

DATED : February 18, 1992

INVENTOR(S) : Hector F. Deluca et al.

It is certified that error appears in the above-identified patent and that said Letters Patent is hereby corrected as shown below:

Claim 12　　　　　　　Delete "(S)" and substitute therefore
Column 12, Line 23　　--- (S) ---

Signed and Sealed this

First Day of June, 1993

Attest:

MICHAEL K. KIRK

Attesting Officer　　　　Acting Commissioner of Patents and Trademarks